(12) United States Patent
Kelrich et al.

(10) Patent No.: US 11,351,111 B2
(45) Date of Patent: Jun. 7, 2022

(54) CONTROLLED RELEASE CAPSULE

(71) Applicants: David Kelrich, Ramat Hasharon (IL); Itzhak Pomerantz, Kefar Sava (IL)

(72) Inventors: David Kelrich, Ramat Hasharon (IL); Itzhak Pomerantz, Kefar Sava (IL)

( * ) Notice: Subject to any disclaimer, the term of this patent is extended or adjusted under 35 U.S.C. 154(b) by 444 days.

(21) Appl. No.: 16/342,693

(22) PCT Filed: Oct. 16, 2017

(86) PCT No.: PCT/IB2017/056416
§ 371 (c)(1),
(2) Date: Apr. 17, 2019

(87) PCT Pub. No.: WO2018/073726
PCT Pub. Date: Apr. 26, 2018

(65) Prior Publication Data
US 2020/0046633 A1    Feb. 13, 2020

Related U.S. Application Data

(60) Provisional application No. 62/410,023, filed on Oct. 19, 2016.

(51) Int. Cl.
| A61M 31/00 | (2006.01) |
| A61K 9/00 | (2006.01) |
| A61K 9/48 | (2006.01) |
| H01F 7/02 | (2006.01) |

(52) U.S. Cl.
CPC .......... *A61K 9/0009* (2013.01); *A61K 9/0053* (2013.01); *A61K 9/4808* (2013.01); *A61M 31/002* (2013.01)

(58) Field of Classification Search
CPC .. A61K 9/0009; A61K 9/0053; A61K 9/4808; A61M 31/002
See application file for complete search history.

(56) References Cited

U.S. PATENT DOCUMENTS

| 3,659,600 A | 5/1972 | Merrill et al. |
| 6,551,234 B1 * | 4/2003 | Martello |
| 8,776,802 B2 | 7/2014 | Mathiowitz et al. |
| 2006/0015088 A1 | 1/2006 | Andrae |
| 2013/0303847 A1 | 11/2013 | Sitti et al. |

FOREIGN PATENT DOCUMENTS

| WO | 0178836 A1 | 10/2001 |
| WO | 2010142284 A2 | 12/2010 |

OTHER PUBLICATIONS

Zhang et al. (Nature Materials, Published Jul. 27, 2015, pp. 1065-1071) (Year: 2015).*

* cited by examiner

*Primary Examiner* — Alma Pipic
(74) *Attorney, Agent, or Firm* — J.A. Lindeman & Co. PLLC

(57) ABSTRACT

This invention teaches a system and a method to control the dispensing of swallow able medicine at the desired flow rate and in the desired location of the gastro-intestinal tract.

19 Claims, 14 Drawing Sheets

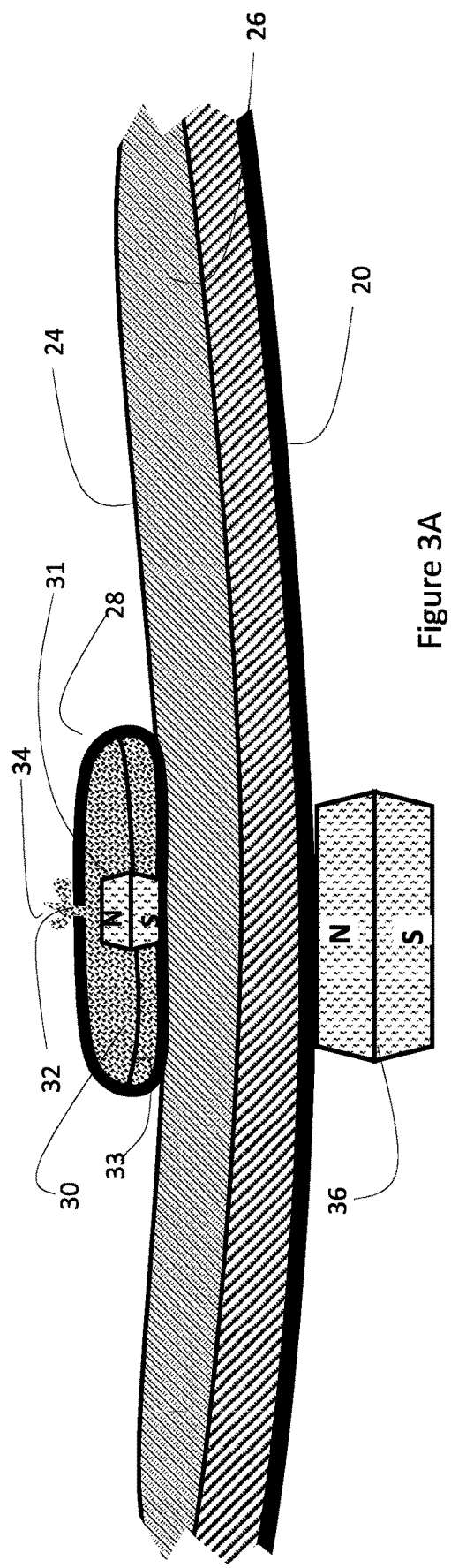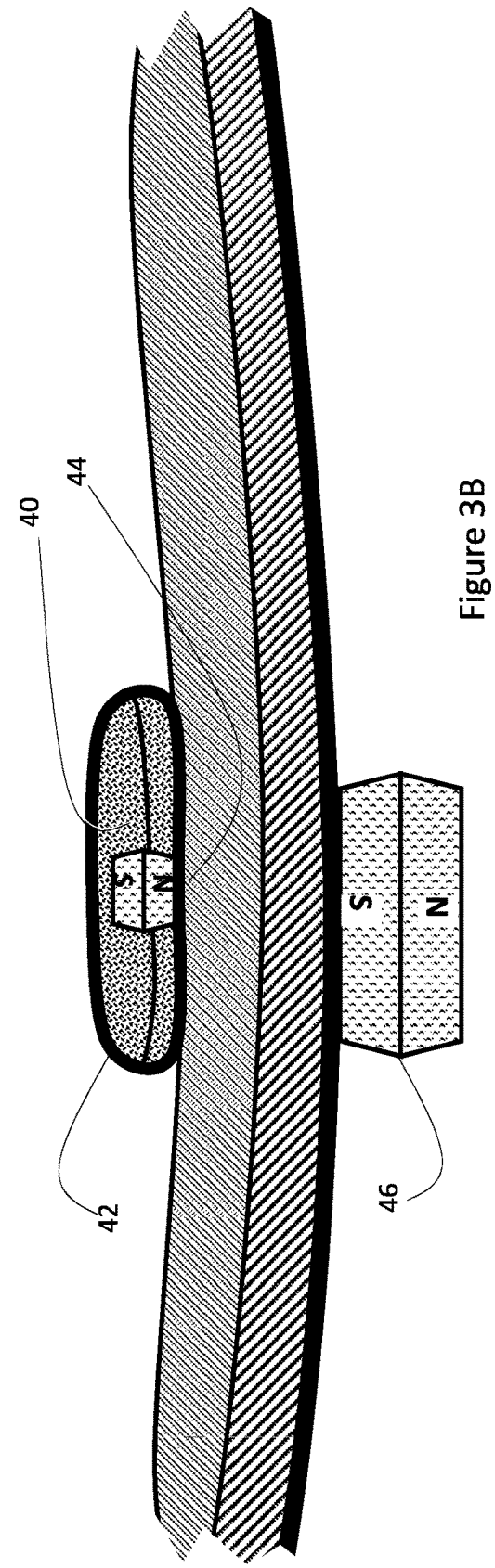
Figure 3A
Figure 3B

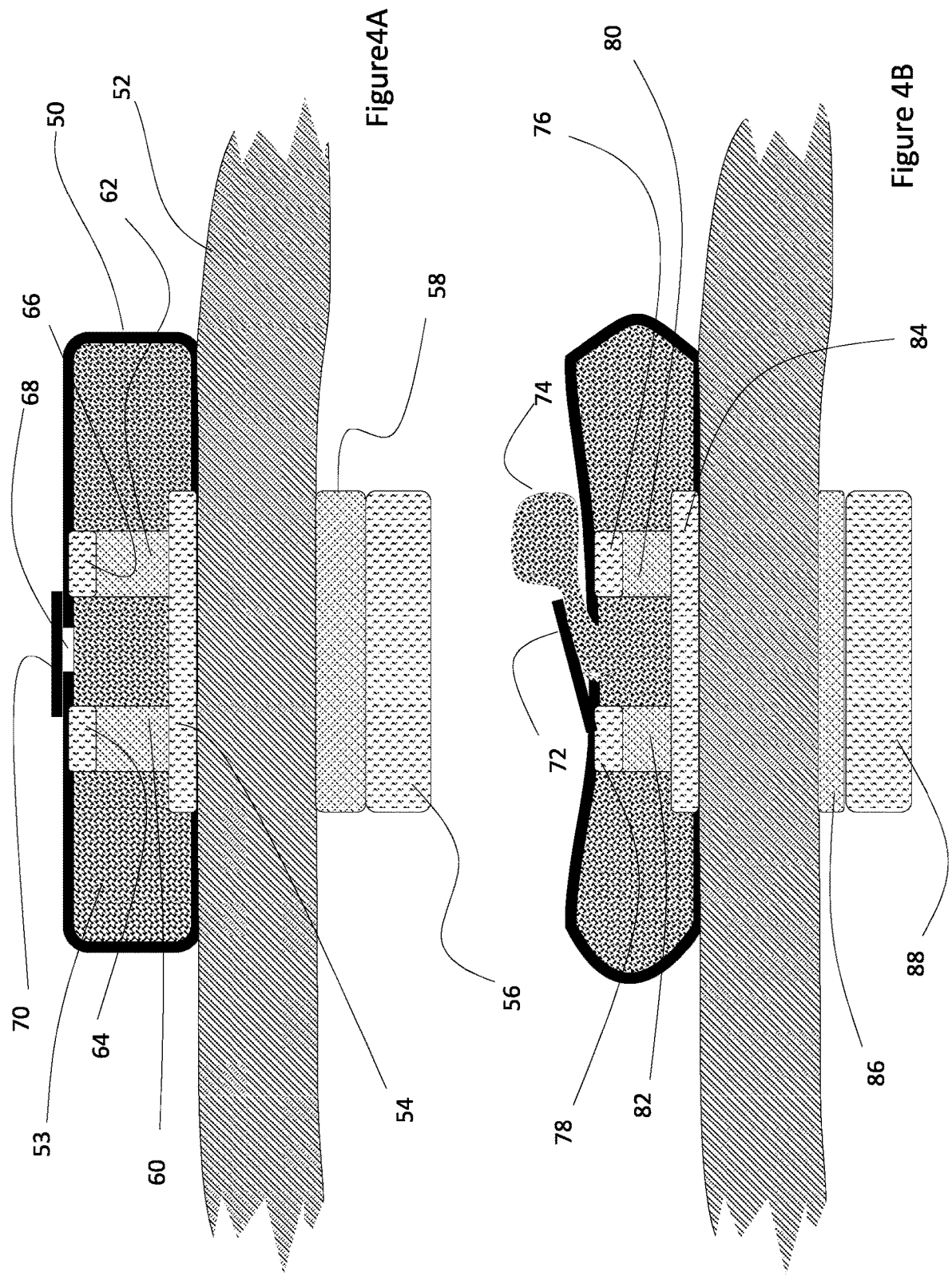

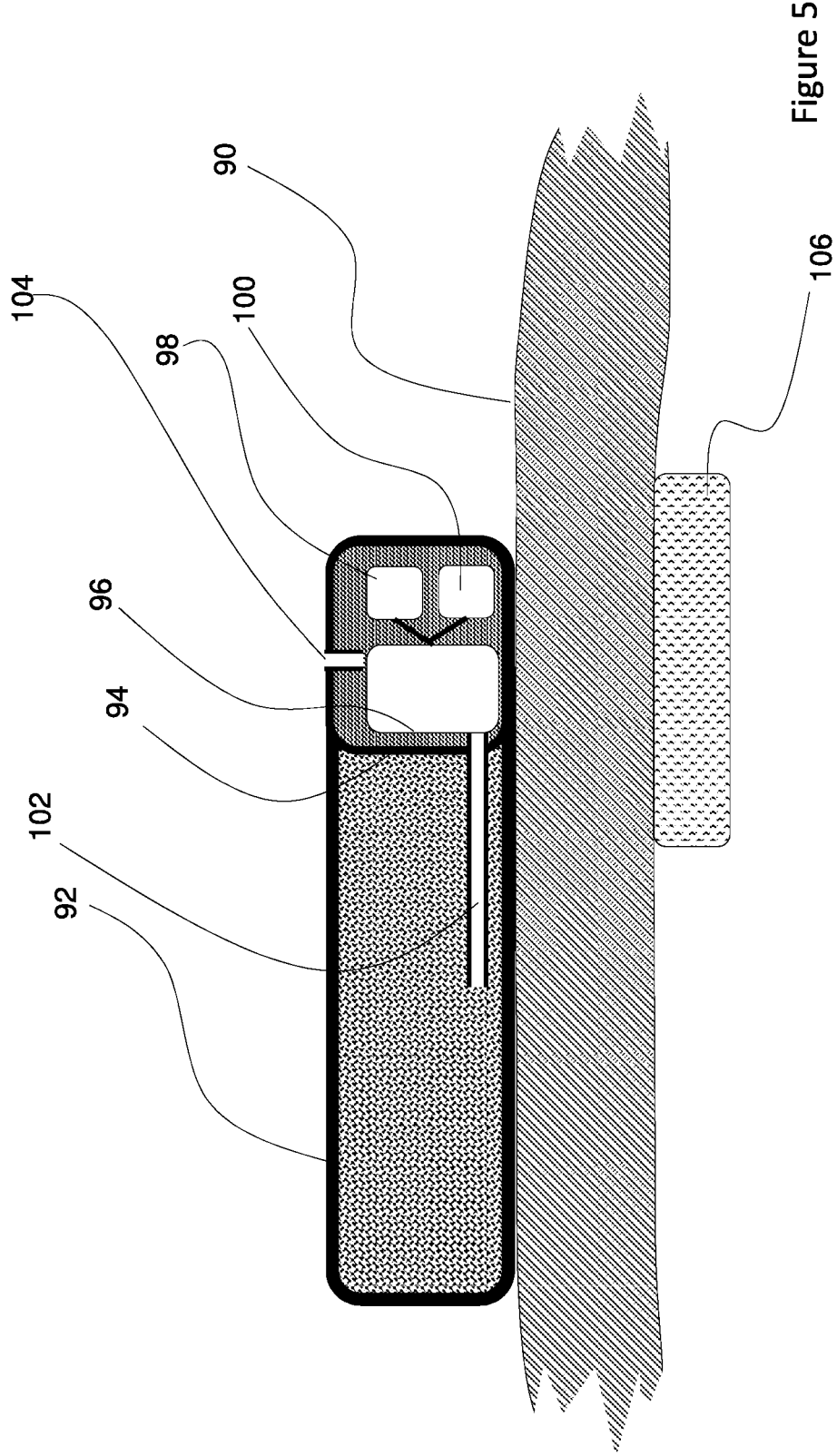

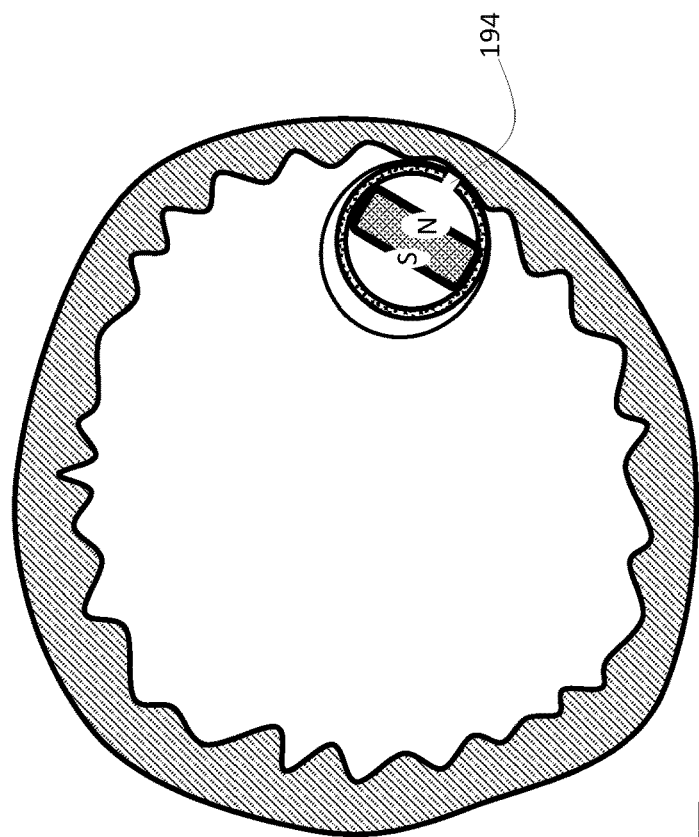
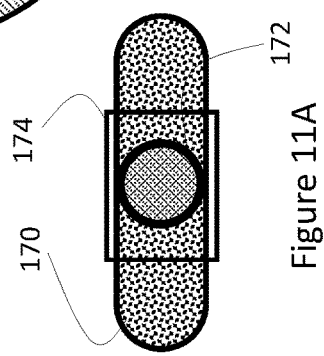
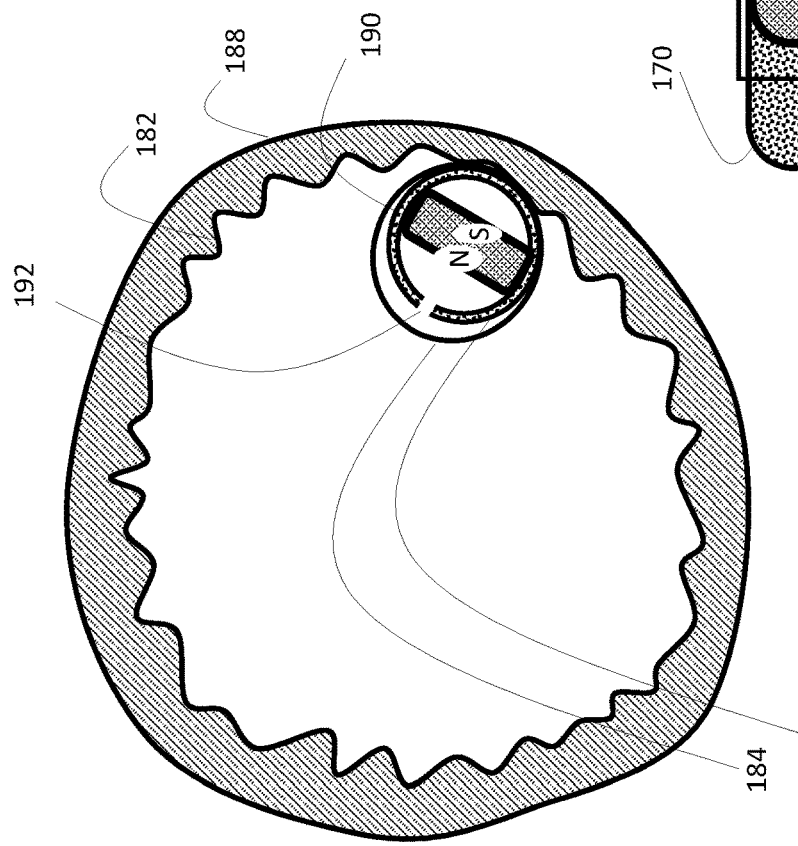
Figure 11C
Figure 11A
Figure 11B

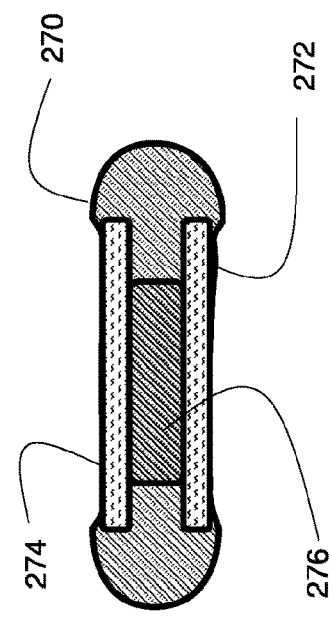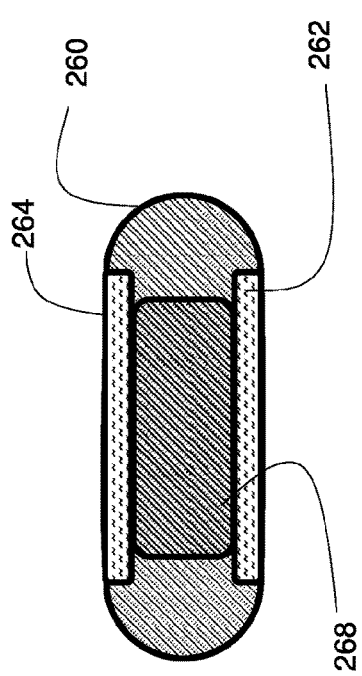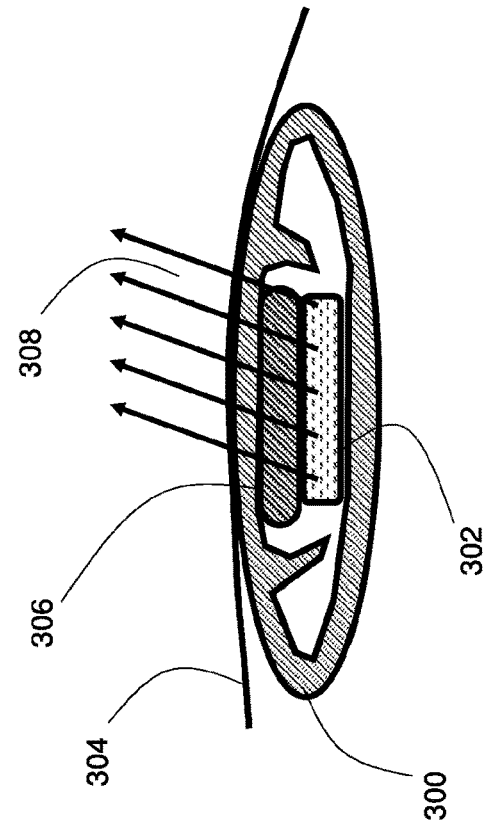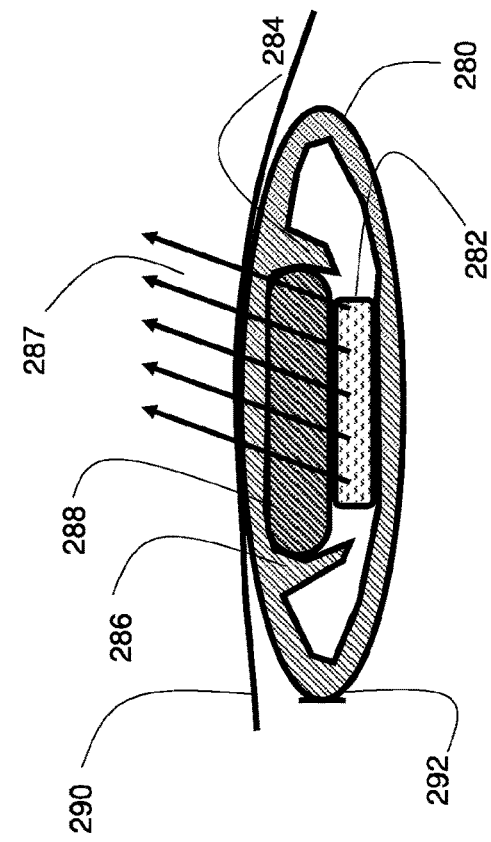
Figure 14B
Figure 15B
Figure 14A
Figure 15A

CONTROLLED RELEASE CAPSULE

DEFINITION OF TERMS

GI—gastro-intestinal tract

Capsule—a swallow-able container that can contain a medicine in a form of one or more pills, gel, fluid or powder. The capsule can be hermetic or perforated, open-able or sealed, made of material that dissolves in water and acid or of material that is not soluble in water and acid.

BACKGROUND OF THE INVENTION

Many types of medicine are consumed by swallowing a capsule that contains the medicine in form of a rigid pill or powder or gel or fluid. A typical example is the Nurofen liquid capsules seen in FIG. 1.

In certain types of medicine, it is important that the capsule stays in the GI and releases the medicine at a slow rate. Some solutions have been suggested in the prior art to keep the capsule in the stomach for a longer time than it would naturally stay there. An example of such a method is found in the "accordion pill" offered by Intec, in Israel, and illustrated in FIG. 2. The capsule is shown in a closed format 18 as it is swallowed, and in a spread out format 19 as it is captured in the stomach. While spread out, the capsule cannot exit the stomach and the medicine that is welded to the wings of the accordion is slowly released until it is consumed, and then the wings disintegrate and are disposed of naturally. As the location of the medication source is mechanically determined, it has to be in the stomach and blocked by the sphincter. The stomach is not an optimal location for the release of the medicine as the stomach acids consume part of it. It would be much better—for some important medications—to have the medication released in the duodenum, where acidity is much lower and transport from the GI to the blood circle is faster. Unfortunately, there is no way to capture the Intec capsule there, as the sphincter is narrower than the duodenum.

Another method of keeping the capsule in the stomach for longer than natural is described in U.S. Pat. No. 8,776,802. In this patent, a method is disclosed for retaining a capsule in the stomach by including a magnet or a ferromagnetic material in the capsule, and applying a strong magnetic force from outside the body. The magnetic force can be used to drag the capsule along the gastro-intestinal (GI) path to a desired location.

However, in all prior art solutions the flow of drug out of the capsule cannot be regulated per the need. There is no control over the rate of dispensing the medicine from the capsule to the GI. The flow of medicine is only dependent on chemical properties of the therapeutic agent contained in the capsule and the amount of medicine left. It is initially high, and as time passes and the amount of medicine in the capsule reduces, the flow rate decreases without possibility to control it.

In some medical situations, such as Parkinson's Disease, there is a preferred rate of supply of medication, and it should be increasing and decreasing according to the state of the patient's body, the content of the stomach and the time of the day. It would be very desirable to have a magnetic capsule that is kept in its place by external magnetic force as taught, for example, by U.S. Pat. No. 8,776,802 but having means for controlling the flow rate of the medicine. Unfortunately, there is no teaching how this can be achieved.

SUMMARY OF THE INVENTION

The present invention teaches a magnetic capsule that can be retained in a desired location in the GI and its release flow can be controlled by manipulation of the retaining magnetic force.

Some embodiments of the invention are unique in the sense that there is no active components and battery in the capsule—making it safer and less expensive.

The retaining of the capsule to the desired location is done by capturing a permanent magnet embedded in the capsule by a magnetic field induced from outside the body.

The flow of the medicine from the capsule into the stomach or into the GI is done and controlled by one of few embodiments in which changes in the external magnetic field cause controllable changes in the flow.

LIST OF DRAWINGS

FIGS. 3A and 3B show a magnetic pill in its two stable states

FIGS. 4A and 4B show another type of magnetic pill in its two stable states

FIG. 5 show a pill that comprises a pump.

FIG. 11A-11C show a capsule with a sleeve for dealing with the interior surface of the duodenum.

FIGS. 14A, 14B show a cross section of a double magnet configuration

FIGS. 15A, 15B show a cross section of a pill retaining configuration

DETAILED DESCRIPTION OF THE DRAWINGS

Figure 1:
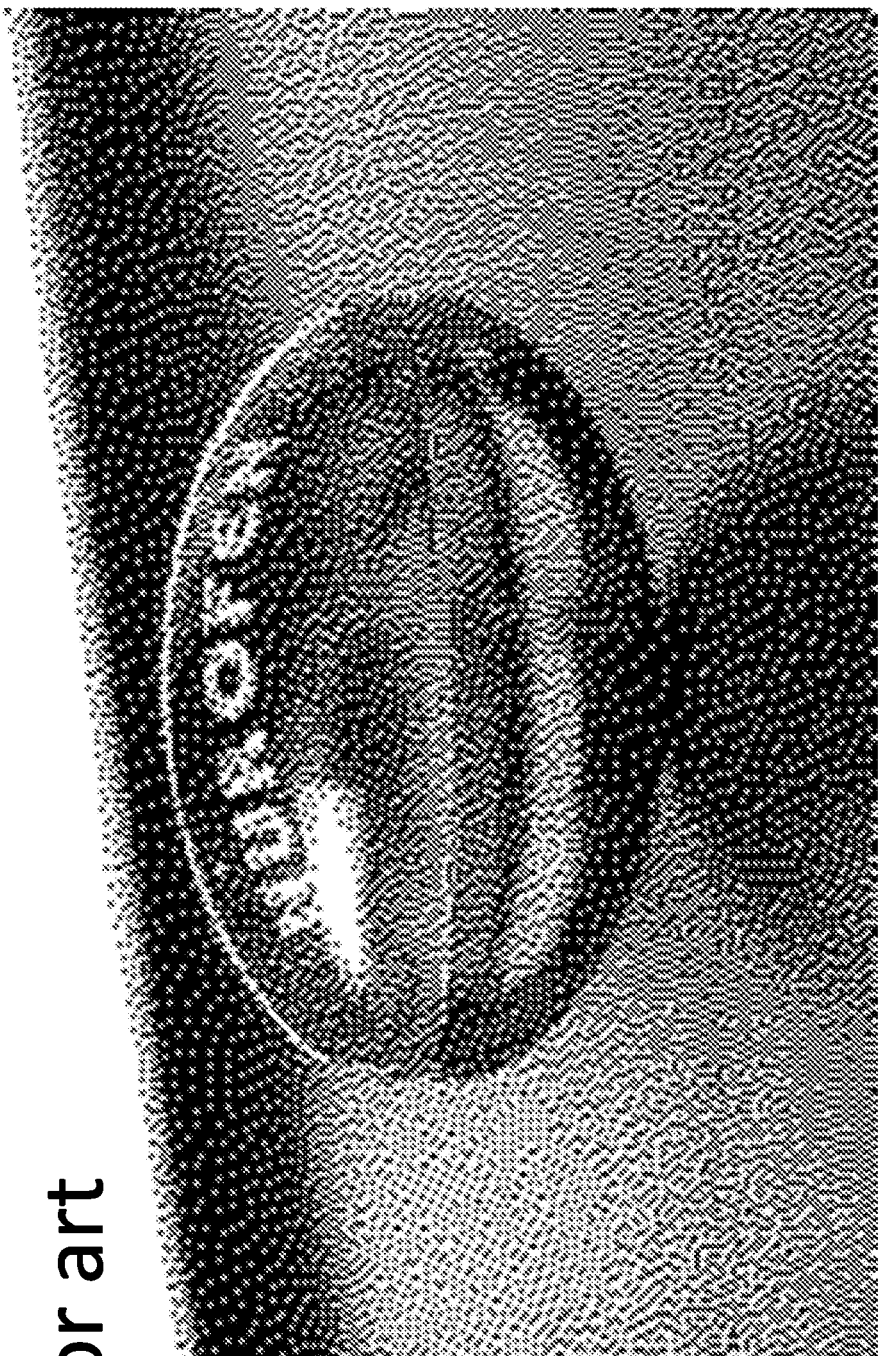
FIG. 1 shows a prior art gel filled capsule.

FIG. 1 shows a prior art gel filled medicine such as Advil or Nurofen.

Figure 2:
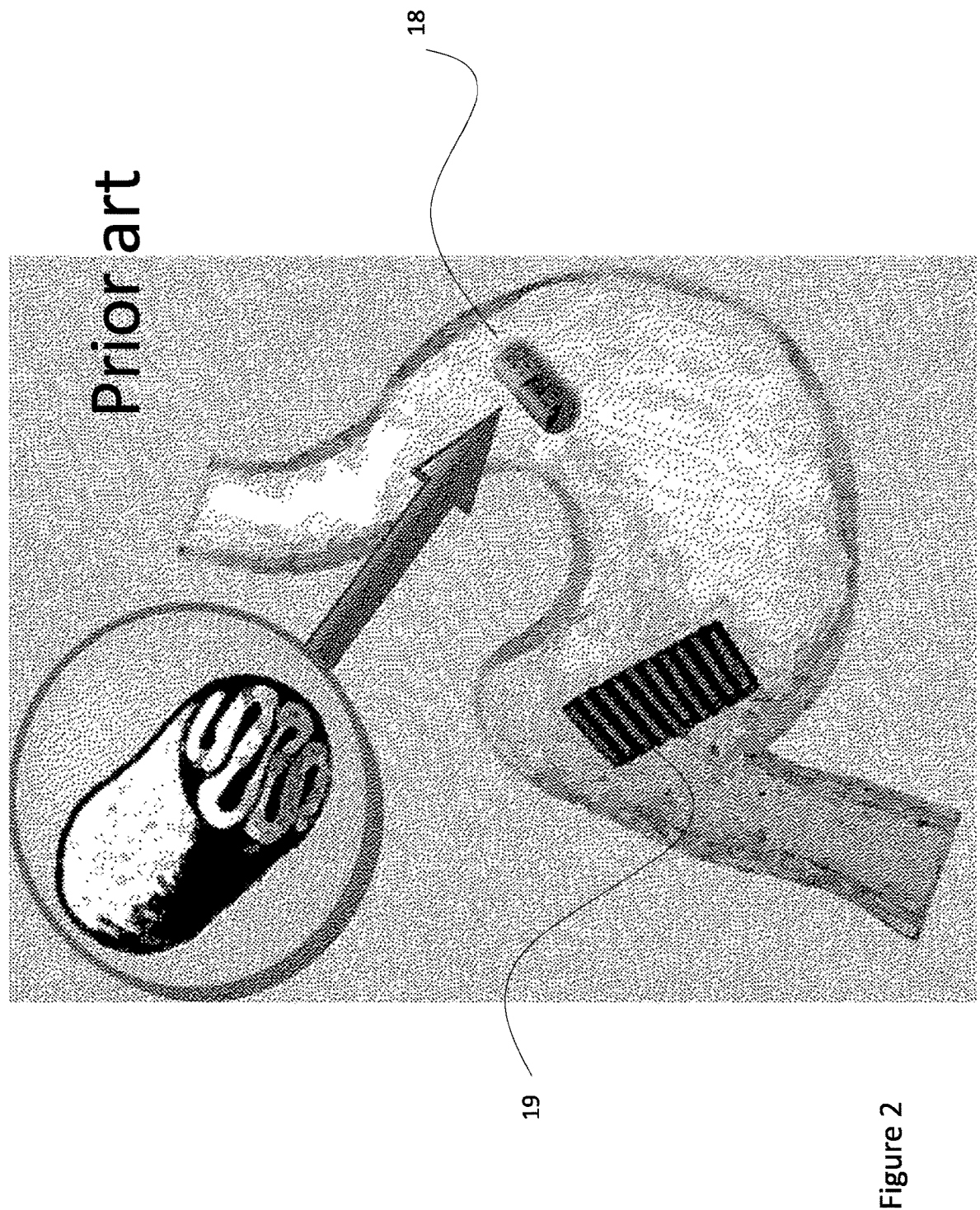
FIG. 2 shows a prior art of a pill with mechanism for retention in the stomach

FIG. 2 shows a prior art capsule of Intec, comprising a spreading carrier of a medicine. The carrier is tightly packed inside the capsule. When the capsule dissolves in the stomach, the carrier spreads out to a size that cannot pass the stomach sphincter and stays in the stomach while the medicine that is spread over it slowly dissolves into the stomach fluids. After a pre-determined amount of time, the carrier dissolves and breaks into small pieces that leave the body naturally.

FIG. 3 shows a capsule 28 shaped like a flattened container and made of a polymer that does not dissolve in the GI, of a size that can easily pass out of the stomach through the sphincter, comprising gel 30 and a permanent magnet 31 suspended on a perforated membrane 33 so that it can reach the ceiling and the floor of the capsule, but not move laterally on a horizontal plane.

A permanent magnet 36 is attracting the magnet 33. The capsule cannot reach magnet 36 as the GI wall 26 and the fat and skin 20 around the GI separate between the two magnets.

The external magnet 36 is held with its north magnetic pole towards the skin 20. This causes the internal magnet 33 to orient itself so that its south pole faces the skin and the external magnet. The magnet 33 is attracted to the external magnet so it moves down to the floor of the capsule, and the capsule is retained tight to the wall of the sphincter or the wall of the stomach (According to the position of the external magnet)—all in order to minimize the distance to the strong external magnet.

A small hole 32 at the top of the capsule, which is the center of its ceiling, allows gel 30 to diffuse out of the capsule and into the GI fluid. In this stable state, the gel is slowly flowing out of the capsule by diffusion.

When the user wants to stop the flow of the gel, he turns the external magnet up-side down, as is shown in FIG. 3B.

FIG. 3B shows the external magnet 46 turned over, so that its south pole is facing the skin. The internal magnet 42 will be flipped over, so that its north pole is facing the GI wall and the external magnet. Due to the membrane, the internal magnet flips over the whole capsule, and then is pressed onto the floor of the capsule, that was the ceiling in FIG. 3A.

The internal magnet 44 is now sealing the hole and is blocking the way of the gel 40, and no gel can flow out of the capsule into the GI. This state is also stable, and will prevail as long as the external magnet is held with its south pole towards the skin.

Whenever the user, or an automatic control system, wants to allow the gel to flow from the capsule into the GI or the stomach, the external magnet is turned with its north pole towards the skin.

Whenever the user, or an automatic control system, wants to block the gel from flowing from the capsule into the GI or the stomach, the external magnet is turned with its south pole towards the skin.

When the capsule empties, the user can remove the external magnet from the skin. The empty capsule will than lose the retaining force and will be carried out of the body.

It should be clear that the trapping location is quite flexible and depends on the location where the external magnet is held. If the need is to release the medication in the stomach, it can be a concave area just above the sphincter. If the need is the duodenum, then it can be point along the duodenum facing the front of the user. For medications that become less effective from acidity, the best place is the duodenum where the acidity of the stomach is compensated by the bile fluid generated by the gallbladder and added to the GI near mid-way along the duodenum.

FIG. 4A shows a capsule 50, essentially similar to the capsule of FIG. 3A. It contains gel 53 and has three permanent magnets. A main large one 54, covering most of the floor of the capsule, and two secondary small ones 64, 66, attached to the ceiling of the capsule and located on two foam pieces 60, 62 that are connected to the floor of the capsule and act like loaded springs. A permanent magnet 56 attracts all three magnets towards the GI wall 52. The external magnet is separated from the skin by a layer of foam 58 that also acts as a loaded spring. In the steady state, the force applied by the external magnet on the internal magnets is sufficient to capture the capsule as it moves by, to retain it to a pre-selected place near the stomach exit and to slightly compress the three springs 60, 62 and 58.

In this steady state, there is no flow of gel from the capsule into the GI.

At the center of the flat ceiling of the capsule there is a hole 68. The hole is covered by a flexible, typically square flap 70 that is connected to the ceiling along one of its four sides. This connection is flexible and can serve as an axis for the flap to slightly open under upwards pressure. The flap is significantly larger than the hole, so that when there is no upwards pressure the hole is sealed by the flap.

Attention is now called to FIG. 4B.

When the user depresses the external magnet 88 towards the body, the spring 86 is slightly depressed and its thickness is reduced. This increases the magnetic force induce on the three magnets inside the capsule. The larger internal magnet 84 cannot move due to the increased force, as it is not sitting on a spring. However, the two smaller magnets, 76 and 78, will slightly move towards the floor of the capsule due to the increase in magnetic attraction, against their springs 80 and 82. In moving down, the two small magnets will pull down and lower the ceiling of the capsule, as they are attached to the ceiling.

The lowering of the ceiling will slightly reduce the volume of the capsule, and the pressure of the gel will increase. The only way for the gel to relieve this pressure is to press upwards on the flap 72 and push it upwards, allowing a small amount of gel 74 to escape from the capsule into the GI.

When the user relieves the pressure on the external magnet 88, the magnet is pushed back to its original position by the spring 86. The distance between the magnet 88 and the two magnets 76 and 78 increases. The attraction force on these two magnets decreased. The springs 80 and 82 slightly push the magnets up and back to their original position. The volume of the capsule begins to increase, and the gel is not pushed out anymore. The flap closes due to the elasticity of its axis.

In this state, no gel is flowing out of the capsule.

Upon the next depression of the magnet 88, the process will repeat, and another dose of gel will be dispensed into the GI. The magnet 88 can either by depressed manually by the user or automatically be a closed loop control system.

The mechanism of FIGS. 4A and 4B is essentially a pump, operated externally and dispensing uniform doses of gel from the capsule into the GI.

Attention is now called to FIG. 5.

While the present invention teaches a unique gel delivery system that does not require the capsule to be active and consume current, there is an alternative embodiment in which the invention is only used to capture the capsule and retain it to a desired place, and the delivery of the gel is done by a miniature pump that is electrically operated.

External magnet 106 is used only to capture the capsule 92 by attracting a permanent magnet 94 and retain it to the desired place. As miniature pump 96 is pulling gel from the volume of the capsule via intake tube 102, and is pushing it out of the capsule and into the GI via an output tube 104. A battery 98 supplies power to the pump and to an electronic circuit 100 that communicates with the controller of the system and drives the pump on demand from the control system.

In this specification the inventors have described some possible embodiments for methods to control the flow of the fluid or gel out of a capsule into the GI, while the capsule is magnetically retained to its place.

In order to teach a complete closed loop control system, we must show possible ways to close the loop by monitoring the effect of the medication on the user.

One simple way to close the loop is by relying on the feeling of the user, enabling him to add a dose of the medicine to his GI whenever he feels the need. This can be done by flipping the external magnet as in FIG. 3A-3B, or by depressing the external magnet as in FIG. 4A-4B.

Another embodiment of a control system relies on measurable physiological signals that reflect the effect of the medication, such as the movement, acceleration and tremor of the user's body and arms. These symptoms increase when the medication effect fades away, and measuring them can provide an indication for extracting a new dose of medicine from the capsule.

Figure 6:
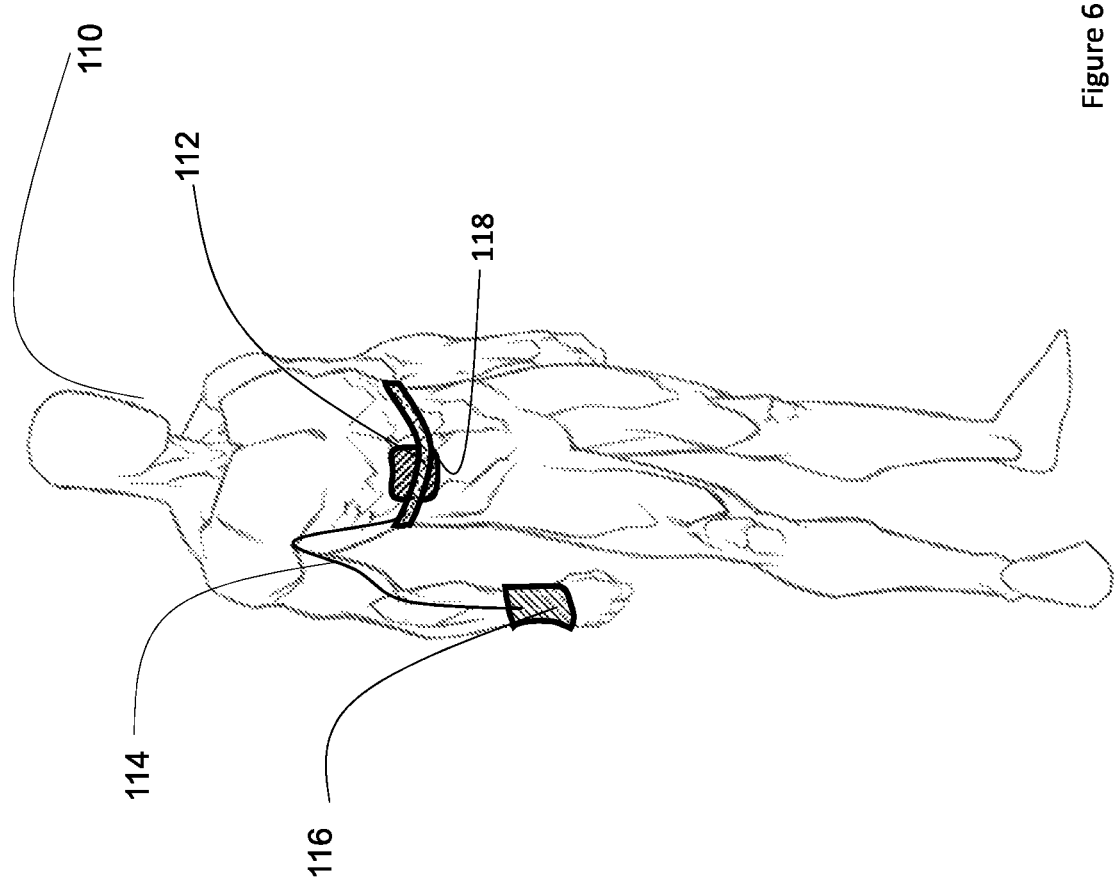
FIG. 6 shows an embodiment of a closed loop system

Attention is now called to FIG. 6. A user 110 has an external magnet device 112 comprising a processor and a mechanical driver held against the duodenum area of his GI by a belt 118. A sensor comprising accelerometers and inclinometers 116 is wrapped around the user's wrist and connected by an electric cable to the device 112. The user swallows a magnetic capsule that makes its way down the GI and is captured by the induced magnetic field of the magnet and is held against the GI wall in the duodenum area. The sensor 116 sends the signals that represent the mechanical motion of the user's arm to the processor in the device 112 via a connecting cable 114. All these components of the system are hidden under the user's clothes (not shown). When the processor detects mechanical symptoms that indicate that the medication level in the user's blood is too low, the processor sends a command to the driver to cause the capsule in the GI to release another dose of medicine. As the medicine is released in the duodenum area, its full content is diffused into the blood system within a short while, and none of the medicine is neutralized by the stomach acid.

Figure 7B:
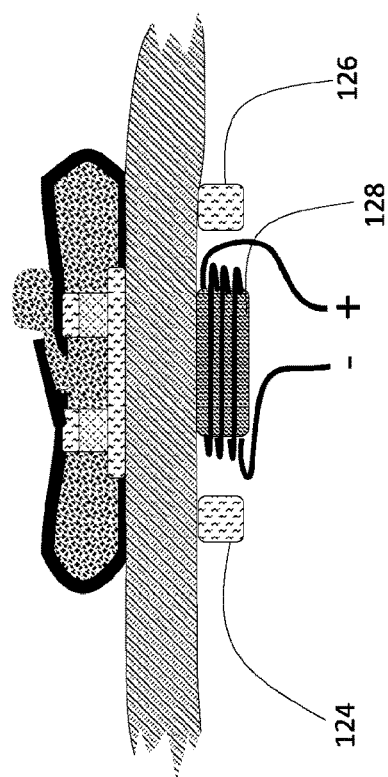
FIGS. 7A and 7B show an electromagnetic version of FIGS. 4A and 4B
Figure 7A:
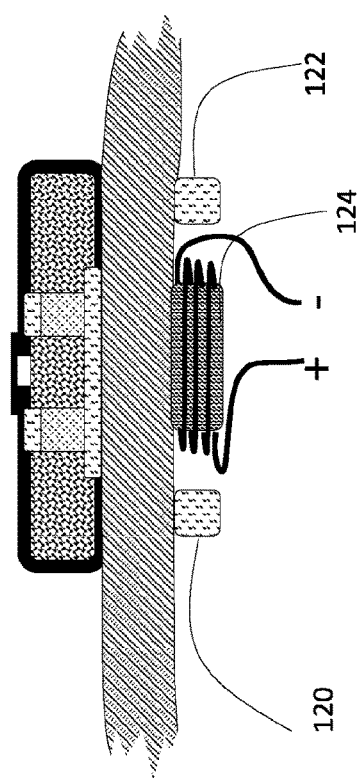

Attention is now called to FIGS. 7A and 7B. These figures show the same mechanism shown and explained in FIGS. 4A and 4B respectively, with the difference that in addition to the external permanent magnets, there is an external electromagnet. In FIG. 4A the electromagnet 124, while the current flows in one direction, is configured to pull the internal magnet and increase the attraction of the permanent magnets 120 and 122. In FIG. 4B the electromagnet 128, while the current flows in the opposite direction, is configured to push the internal magnet and decrease the attraction of the permanent magnets 124 and 126. The electromagnet is configured to create a weaker magnetic field than the permanent magnets, so that the combined magnetic field is always attracting the capsule and keeps it in place—but the decrease and increase of the magnetic field due to the contribution of the electromagnet modulates the magnetic field and enables the delivery of gel out of the capsule as explained in FIGS. 4A and 4B.

This embodiment, where the activation of the controlled delivery of the capsule is electronic rather than mechanical, makes this invention suitable for closed loop control.

In a preferred embodiment, the magnetic attraction is gradually and monotonously increased, to continuously shrink the volume of the capsule and force more drug to squeeze out through the hole.

In a preferred embodiment the hole 68 of FIG. 4A is made small enough to prevent the gel or liquid flowing out spontaneously, but the increase in pressure inside the capsule due to its shrinkage does force some of the fluid to squeeze out.

The same electric mechanism can be applied to the other configurations taught in this application, such as FIGS. 3A and 3B where flipping the capsule can be achieved by changing the direction of the current in the electromagnet.

Figure 8:
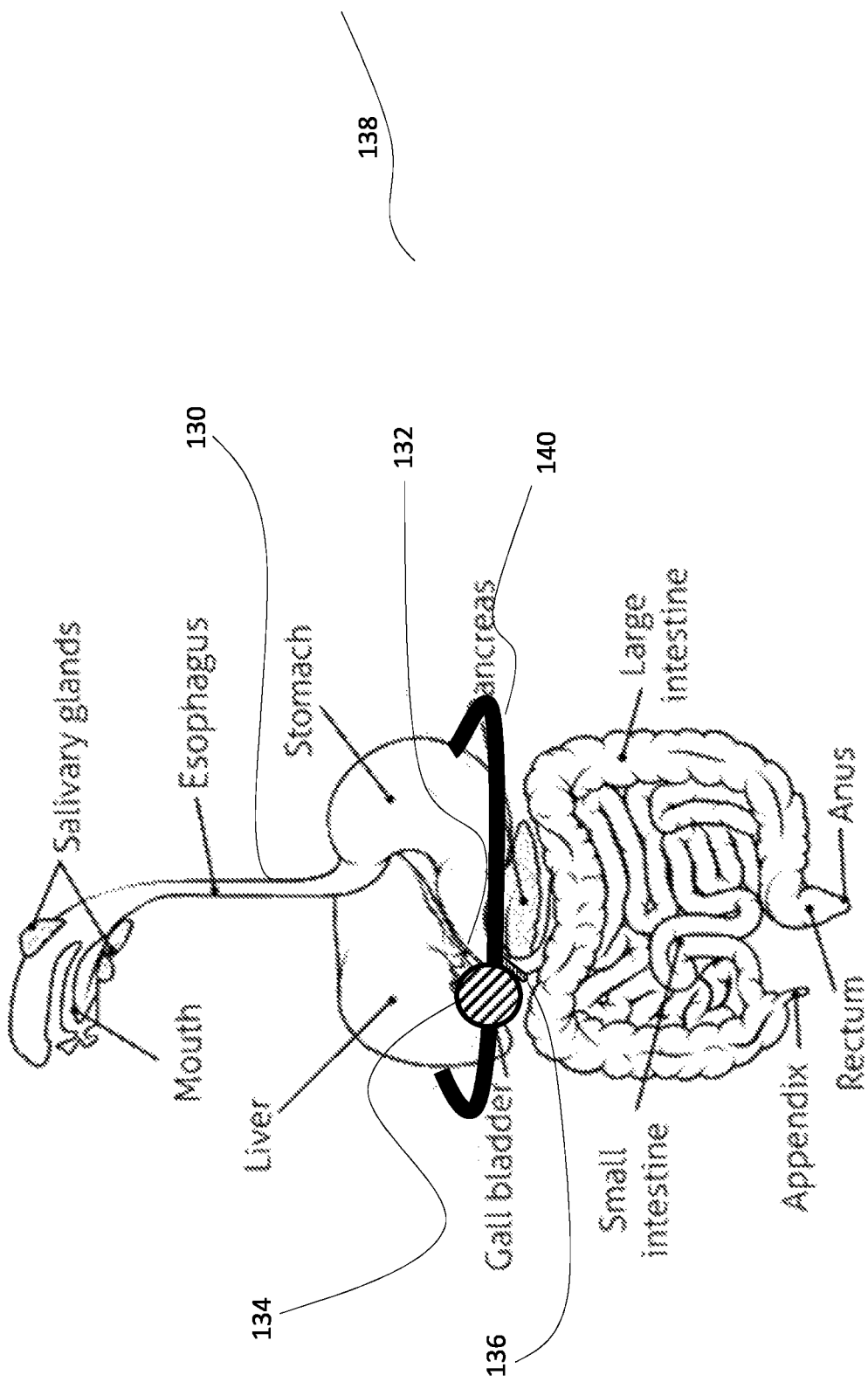
FIG. 8 shows the layout of the capsule and the external magnet on the body

Attention is now called to FIG. 8. Some internal organs of the human body 130 are shown and annotated. The outline of the body is not shown, for clarity.

The user wears a belt 140 around his stomach. The belt carries a device 134 that induces a strong magnetic force, such as a permanent magnet or an electromagnet. The magnet induces a magnetic field around it. A ferromagnetic object within the magnetic field will be attracted towards the device. If the attracted object is located in a convex vessel that has a point of minimal distance to the magnet, the attracted magnet will tend to reach that point and stay there as long as the magnetic attraction prevails.

Figure 9:
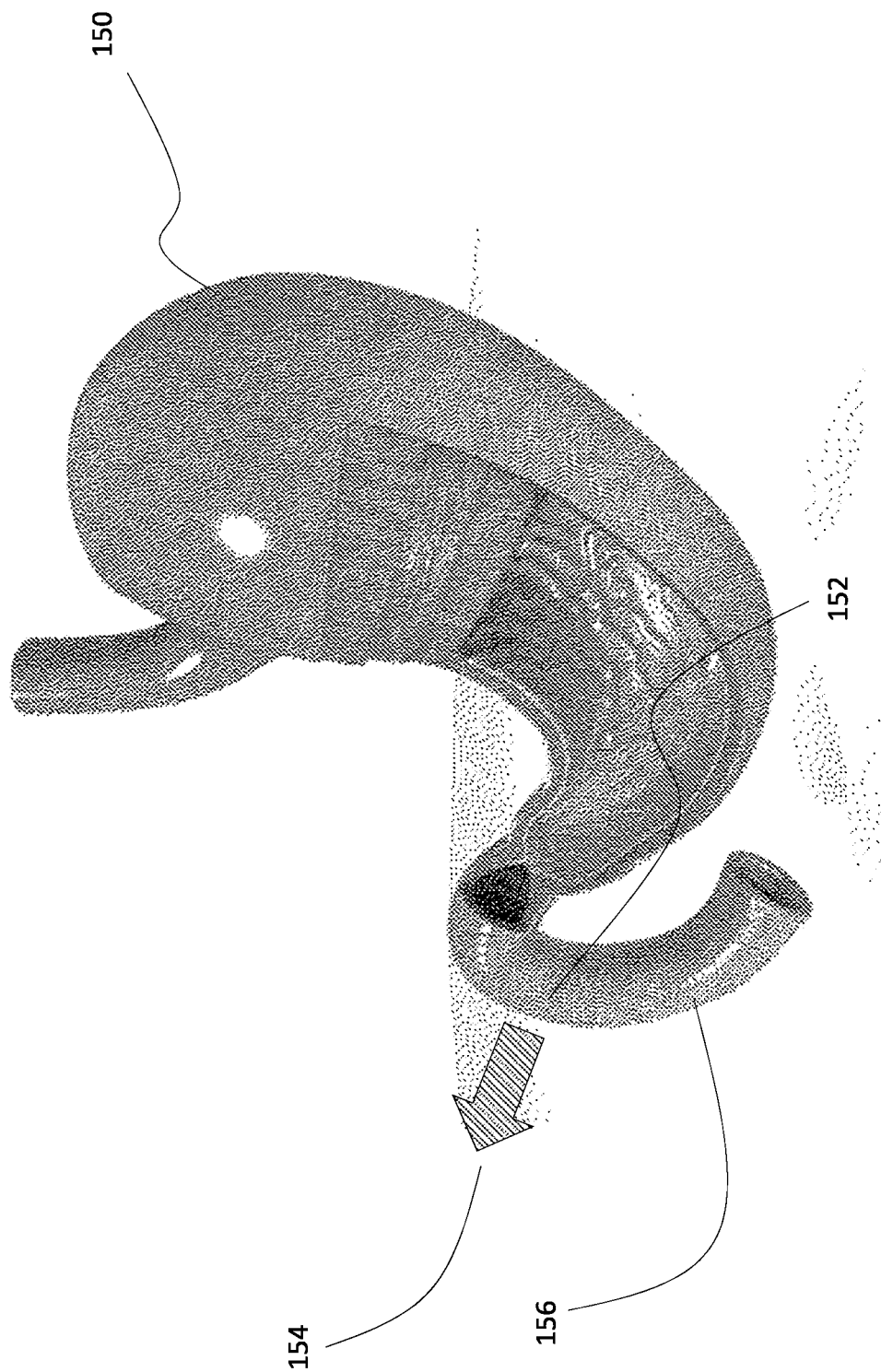
FIG. 9 shows an anatomy of the human stomach.

Attention is now called o FIG. 9. The duodenum 156 connected to the exit of the stomach 150 has a generally convex shape. If the user swallows a capsule comprising ferromagnetic material, and if a magnetic force is induced around the duodenum in the direction shown if reference 154, then the capsule—in passing near area 152—will be attracted by the magnetic field and will adhere to the duodenum wall there. Going back to FIG. 8, the magnet on the belt 140 creates a magnetic field in the right direction—as shown by reference number 154 in FIG. 9. A capsule 136 that is made of a persistent material that is not attached by the stomach acids, will flow with the stomach content through the duodenum and will be captured by the magnetic field and will be trapped in the concave area 152. It should be noted that area 152 is concave from the inside if the stomach, and is convex from the outside, facing the magnet.

While the capsule is attracted to the magnet, it is ready for the operations described in FIGS. 3, 4 and 5 above.

Figure 10:
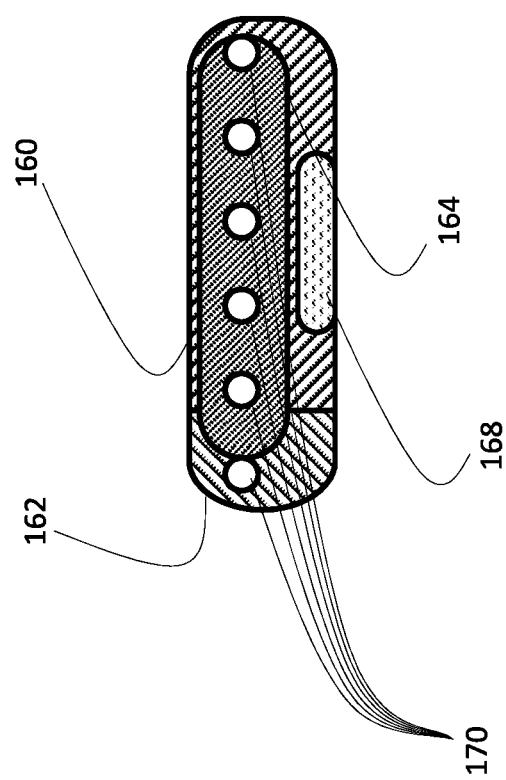
FIG. 10 shows a carrier capsule for slow medication delivery.

In one embodiment, the capsule of the present invention is used as a carrier for a slow-release medication swallowed as a passenger pill or a capsule. In this embodiment, illustrated in FIG. 10, a capsule 160 comprising an elongated wall can be opened by removal of a cap 162. Inside the capsule, there is a permanent magnet or a piece of ferromagnetic material fixed to the elongated wall thereof. The capsule can be swallowed and captured in a desired location in the GI or in the stomach by an external magnet placed at the right place. The user, or the care giver, or the medicine manufacturer can open the capsule and insert a pill or a capsule 164 with any slow-release medication into a cargo space intended to accommodate the size of the passenger pill or capsule. Holes 170 located in the elongated wall of capsule 160 allow GI fluid flow into the capsule 160 and dissolve the medication 164 that then mixes into the GI fluid through holes 170. The carrying capsule 160 can be released after the medication is consumed by releasing the attraction of the external magnet. A magnetic axis of the permanent magnet is perpendicular to a longitudinal axis extending through the capsule 160. The longitudinal axis extending through the capsule 160 is parallel to the elongated wall thereof. As used herein, the term "elongated" refers to a capsule having a long dimension (e.g., length) which is greater than any short dimension (e.g., width or diameter) thereof.

In a preferred embodiment of the system, the external magnet is an electropermanent magnet. This type of magnet is well known in the art and is offered by Magma, in Kibbutz Gesher in Israel. They are a permanent magnet which is partially wound by electric wire. When no current flows in the wire, the device acts as a permanent magnet. When current flows in the wire, then the permanent magnetic field is intensified or reduced—depending on the direction of the current. In a special case, the permanent magnet can be totally neutralized by the current. In this invention, alternating current in the wires of electro permanent magnets is used to modulate the magnetic attraction on the pill.

In one embodiment, the magnetic field is modulated at a low frequency causing the capsule in the GI to vibrate in response to the modulated attraction. As the tissue of the GI wall has some elasticity, an increase of the magnetic attraction causes the capsule to slightly move towards the external magnet, and a decrease of the magnetic attraction causes the capsule to slightly move back from the external magnet due to the spring action of the GI wall—but the bias attraction of the capsule to the external magnet is still there, keeping the vibrating capsule in place.

In one embodiment the external magnet is modulated at a predetermined frequency, and a vibration sensor such as a microphone, an accelerometer or a vibrometer, is attached to the external magnet listening for synchronized vibration from the GI. The vibration sensor is preferably made of non-ferromagnetic material so that it is not affected by the varying magnetic field but only by the mechanical vibration. Such vibration sensor can be optical microphone as offered by Optoacoustics LTD. From Moshav Mazor, Israel or non-ferromagnetic piezo electric transducer.

If there is no captured capsule in the GI, the vibration sensor will not pick any signal. This will be an indication that there is no capsule anchored in the GI.

If there is a captured capsule in the GI, the modulation of the magnetic field will cause the capsule to slightly vibrate at that frequency, and the vibration sensor, being very close to the capsule with a fluidic material connecting them, will pick up that signal. As the vibration sensor picks the vibration signal before the capsule is close enough to the external magnet to be captured, the system provides an early warning to the user on the approaching capsule. Such response signal indicates that there is a capsule approaching. The user can then adjust his pose, posture or activity to ensure the capture of the capsule when it arrives at the capture point.

The frequency of the electromagnetic signal that is modulating the permanent magnetic field is, preferably, set in the ultrasound range, so that the sound will not be heard by the human ear and not disturb the user or embarrass him in public.

In a preferred embodiment, the capsule comprises an additional, small weight permanent magnet that is elastically attached to the capsule. Such small magnet can vibrate at higher frequencies than the capsule body itself.

The frequency of the electromagnetic signal that is modulating the permanent magnetic field is, preferably, set to the resonance frequency range of the GI in the area of the capsule capture. Such resonance frequency range exists as the GI wall has both elasticity and mass. When the modulated magnetic field has a frequency in that range, then the amplitude of vibration, upon starting the modulation, will gradually increase as energy is added to the vibrating capsule with each cycle of the modulation. The slope of the vibration amplitude depends on the mass of the capsule, and this depends on the amount of gel left in the capsule.

This verification method can be part of the automatic control system, so that if a reasonable amount of time passes since the intake of the capsule by the user and the capsule is not found anchored, it will indicate that the capsule escaped the magnetic attraction an is lost into the GI. In such cases, the user can be advised to take another capsule.

The modulation on the magnetic field can be delivered in pulses and the vibration sensor can determine the time constant of the leading edge and the falling edge of the capsule vibration. As the rate of kinetic energy delivered to the capsule by the modulated magnetic field is constant, the time constant of the rising and falling edges of the vibration of the capsule can give an estimate of the mass of the capsule, thus the amount of medication left in it. This can enable a control system to predict when will the capsule be empty, and to indicate to the user that he should take another capsule. The empty capsule can then be released and the magnetic trap can be re-activated to wait for the new capsule.

In a preferred embodiment, the capsule is surrounded by a sleeve for keeping the delivery hole closed when the capsule is leaning on rough surfaces. Attention is now called to FIG. 11A. A capsule 170 of the type illustrated in FIG. 3A and having one or more holes for delivering the drug, is loosely surrounded by a short sleeve 174 made of elastic material. The sleeve can be welded or glued to the side of the capsule so that the capsule does not slide out of the sleeve.

FIG. 11B shows a cross section of a tube, such as a duodenum 188. The internal wall of the tube 182 is not flat. The illustration shows a cross section through a capsule 186 and the sleeve 184. The cross section passes through a cylindrical magnet 190 fixed to the wall of the capsule. The magnetic poles of the magnet are at the two circular ends. An external magnetic attraction is directed so that the South pole of capsule magnet faces the wall of the tube, and the north pole of the capsule agent faces the center of the tube.

The cross section of FIG. 11B also passes through a delivery hole 192 through which the drug can exit from the capsule into the tube. When the magnet is oriented with its north pole facing the wall, the delivery hole is facing the center of the tube, and the drug is free to flow out, passing between the capsule and the sleeve.

When the external magnetic field is reversed, the magnet 190 flips over, and the explanation is flipped to FIG. 11C.

In FIG. 11C the magnet is shown with its north pole facing the wall of the tube. The delivery hole 194 is facing the wall, but as the wall is not smooth and has protrusions and dents, the hole cannot be tightly sealed. However, as the sleeve is compressed between the capsule and the wall, the delivery hole 194 is leaning the smooth surface of the sleeve, and is well sealed.

In this way the sleeve enables the capsule to function when facing a non-smooth wall, such as the duodenum wall.

Figures 12A, 12B, 12C:
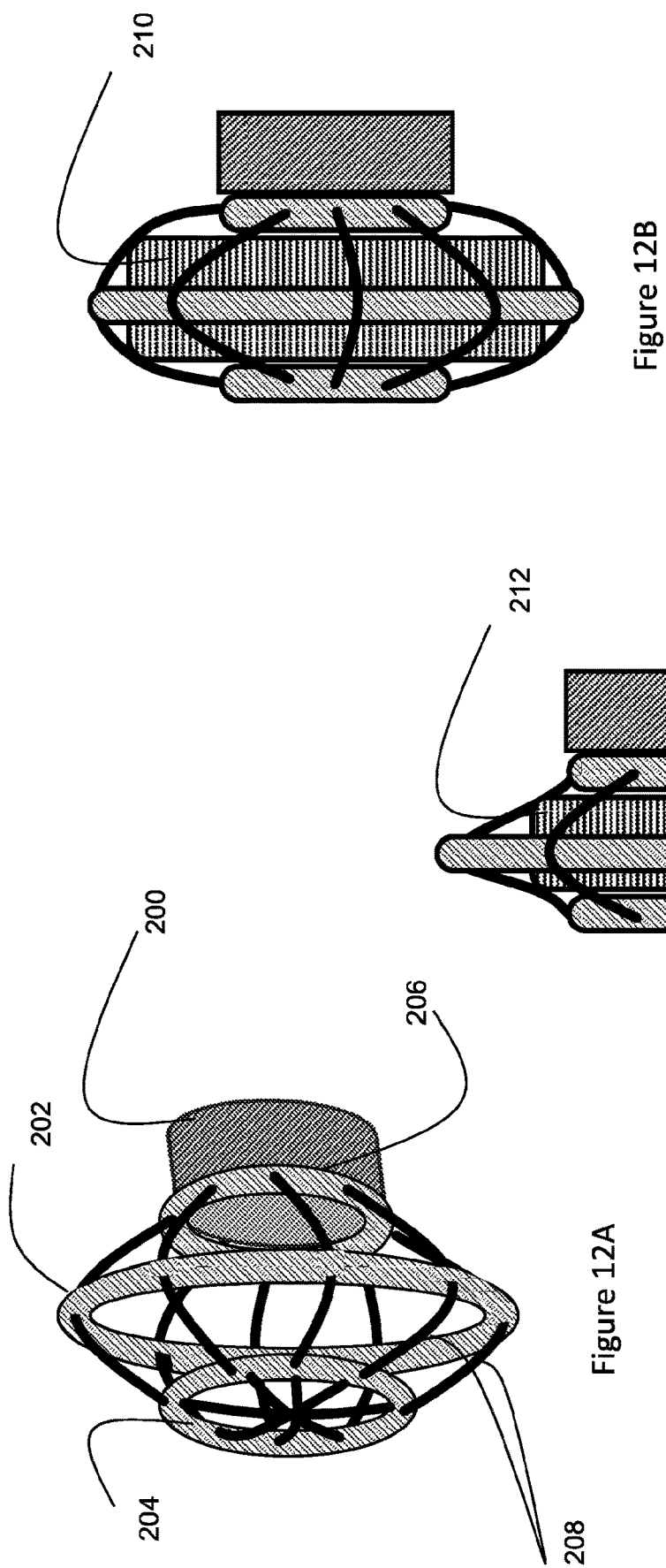
FIGS. 12A-12C show an open, elastic capsule

Attention is now called to FIGS. 12A, 12B and 12C. FIG. 12A shows a permanent magnet 200, typically coated with a bio-compatible coat that is not attached by water or acid in the body, fixed to a ring 206 made of an elastic material such as silicone. 8 elastic straps 208 are coming out of rind 206 at essentially equal spacing and pass through holes in a second, larger, ring 202. The internal diameter of ring 202 made of elastic material such as silicone that can accommodate the diameter of a typical slow release medication pill, and is typically 14 mm. the straps continue through the holes in ring 202 and pass through holes in a third ring 204 made of elastic material such as silicone. All the straps meet near the center of ring 204 and each strap continues as its opposite strap, so that strap 1 continues as strap 6, strap 2 continues as strap 7 etc. The straps continue through the holes of ring 202 until the meet and fix to ring 204. The straps pass through the holes in rings 202 and 204 with some friction.

FIG. 12B shows the mechanism of FIG. 12A where a pill 210 is placed inside the cage of the straps and rings. The user may slide the straps through the holes in order to make an opening between straps that is big enough for the pill to get into the cage, and then can slide the straps back to get a symmetrical cage. The pill Is now firmly held by the cage, yet is open to the environment and can dissolve and release a drug if swallowed.

The pill can preferably be coated by Enteric coating that serves as an isolator that protects the pill until it reaches the duodenum, and then dissolves and releases the drug into the duodenum. By Enteric we mean a coating that is used to cross the stomach (which may take 1 to 3 hours) by being stable at the highly acidic pH in the stomach but breaks in the alkaline environment of the duodenum and the Small Intestine. Enteric coatings are used either to protect the stomach from a drug (Aspirin) or to protect the drug from the stomach (erythromycin).

FIG. 12C shows the mechanism of FIG. 12B after the pill has partially dissolved and consumed. The pill, about half its original size, is still firmly held by the cage due to the elasticity of the straps and the rings.

In a preferred embodiment, the system comprises a mechanism for controlling the magnetic attraction between the external magnet and the capsule. The magnetic attraction should preferably be controlled as too weak attraction may cause the capsule to escape down the duodenum due to gravity or due to food flow from the stomach, while too strong attraction may cause damage to the wall of the GI.

Figure 13A:
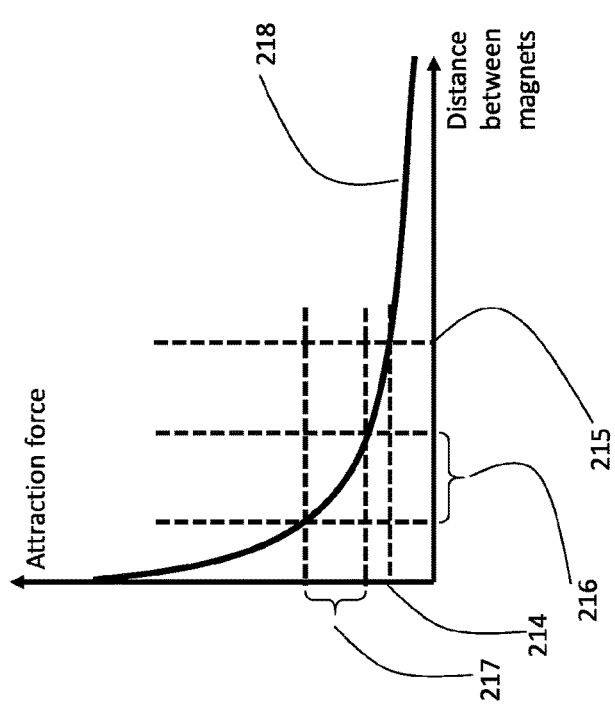
FIGS. 13A, 13B show a mechanism for controlling the magnetic attraction on a capsule.

FIG. 13A shows a typical relationship 218 between the distance and the attraction force of two magnets having a fixed magnetic strength.

The attraction is typically weakening with the square of the distance. At some distance 215 the attraction force 214 is too weak to hold the capsule in place, and the capsule will detach and be lost.

Clearly there is a range of forces 217 that is desirable, not too strong and not too weak. This desired range of forces corresponds to a range of distances 216.

Figure 13B:
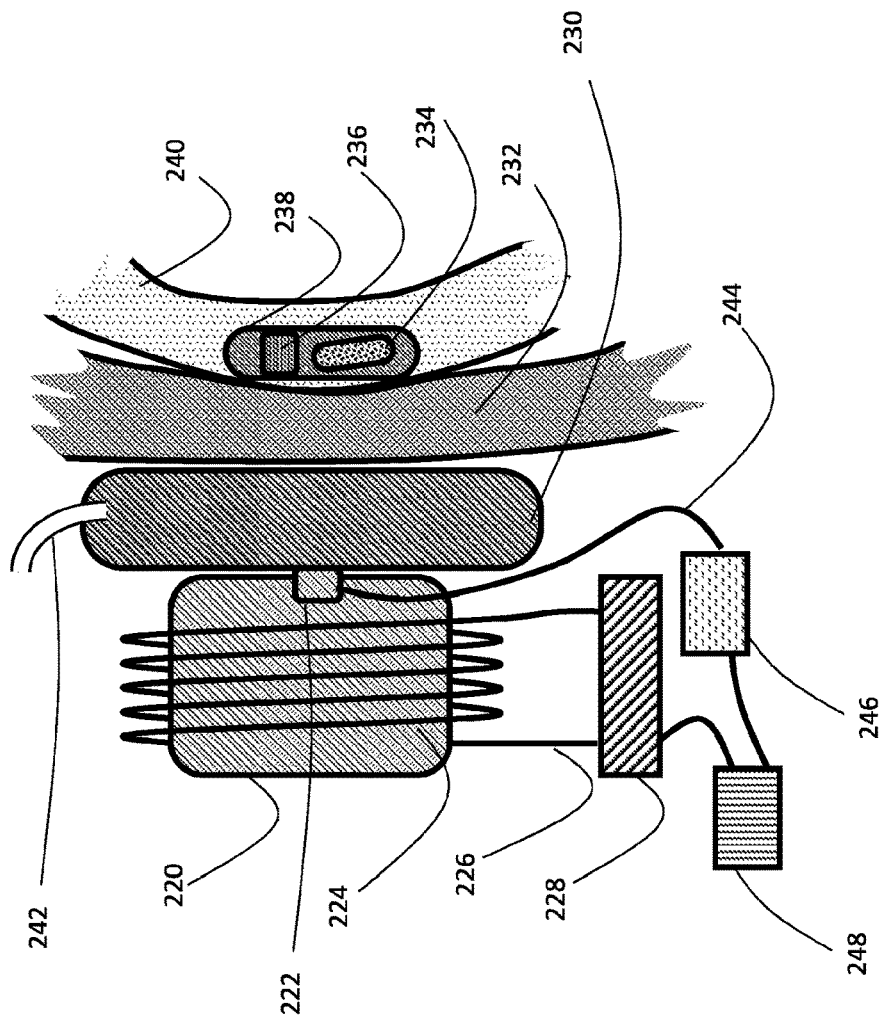

FIG. 13B shows a possible configuration of a system to measure the distance between the external permanent magnet 214 and the magnet 236 in the capsule 238 in the duodenum 232.

Electrical windings 224 around the magnet 220 can increase or decrease its magnetic field, in a process known in the art as "electro permanent magnet" referred to earlier in this application. The windings are connected to a driver 228 through wires 226. The driver generates a sinusoidal signal that is strong enough to increase and decrease the magnetic field of magnet 220 by, typically, 2%-4%. These changes do not significantly affect the position of the capsule 238 or the state of its delivery valve, but cause it to vibrate at the frequency of the sinusoidal current. This frequency can be range between few hundreds of hertz up to tens of kilohertz.

The vibration of magnet 236 due to the periodic changes in the magnetic field are very small, but they can be picked by a sensitive vibration sensor 222, preferable made of materials that are not ferromagnetic so it is not affected by the magnetic field directly—such as a piezoelectric transducer well known in the art as a vibration sensor device. Vibration sensor 222 is connected via wire 244 to a tuned filter and amplifier 246. The signal picked by the vibration sensor will have a phase delay relative to the current in the wires 224 as the sound wave have to cross the distance between the internal magnet 238 and the vibration sensor 222.

If the frequency is 40 KHz, and the speed of sound in the human flesh is 1000 m/sec, then the wave length of the sound in the flesh is 1000/40=25 mm. if the phase difference between the two signals can be measured to an accuracy of 10 degrees, then the distance can be calculated with an accuracy of better than 1 mm.

The driving signal from the driver 228 and the filtered and amplified sound signal from the amplifier 226 are fed to a phase comparator 248, and the phase difference is converted by a processor (not shown) to distance. The distance is then converted using the chart of FIG. 13A to attraction force.

The spacing of the external magnet from the skin, is controlled by a fluid pouch 230 which is a part of the device that the user wears. If the force is too high, fluid is pumped into the pouch through a pipe 242. The separation between the external magnet and the capsule increases, and the attraction force is reduced. If the force is too weak, fluid is pumped out of the pouch and the attraction force increases. This mechanism enables the device of the present invention to suit every user, fat or thin, and every anatomy of the duodenum.

An alternative way to measure and control the attraction force between the two magnets is to insert a strain gauge device between the pouch 230 and the body 232 of the user or between the pouch 230 and the external magnet and measure the compression force before a capsule is captured and after a capsule is captured.

Attention is now called to FIG. 14A. A capsule 260 has two permanent magnets, 264 and 262, configured to have their north poles facing one and the same direction, and their south poles facing one and the same direction. The magnets are attached to the bottom and top walls of the capsule.

A long release solid pill 268 is placed between the two magnets, and as it faces two opposite poles, it is compressed between the two magnets 262 and 264 that are attracting each other.

A magnetic force perpendicular to the magnets (not shown) is attracting the magnets, and the pill, and the capsule body, to one direction. If the capsule is in the GI and the magnetic force comes from a permanent magnet outside the body—the attraction force is towards the wall of the GI as in all the previously disclosed configurations. The capsule does not need to be closed, it can be open at the ends not seen in this cross-sectional view, to ease on the release of the drug to the body.

As the pill dissolves and releases its material to the GI, its physical dimensions are being reduced. Attention is now called to FIG. 14B. The pill 276 is smaller in all dimensions than pill 268, but as the magnets 272 and 274 are still attracting each other, the pill stays firmly gripped between the two magnets and does not escape into the GI. The body of the capsule 270 is elastic and can change it shape as the two magnets are coming closer to each other.

This configuration is instrumental to hold a long term pill in capture until it is fully consumed, and should be considered an alternative to the configurations of FIG. 12.

Attention is now called to FIG. 15A. A capsule 280 contains one magnet 282 attached to the floor of the capsule. External magnetic field 287 created by an external magnet attracts the magnet 282 towards the wall of a GI 290, and the capsule 280 is captured and compressed to the wall 290.

A long release pill 288 is placed above the magnet 282 and is compressed between magnet 282 and the ceiling of the capsule, and is retained in its place by a cylindrical fence that dropping from the ceiling of the capsule and is seen in this cross section in reference marks 286 and 284. The cylindrical fence has a diameter that is slightly larger than pill 288 so that the pill can easily be inserted into its place before swallowing the capsule.

As the pill dissolves and releases drug into the GI, its dimensions shrink. Attention is no FIG. 15B. The pill 306 is now smaller, but as magnetic field 308 continues to attract magnet 302 towards the wall 304 of the GI, the pill is kept in its place and cannot move or escape.

The invention claimed is:

1. A drug delivery system comprising:
   (a) a capsule configured to be swallowed by a user, the capsule comprising: a drug contained within the capsule, at least one internal permanent magnet fixed to an elongated wall of the capsule, and one or more holes located at a first side of the elongated wall of the capsule, wherein a second opposing side of the elongated wall of the capsule is devoid of holes; and
   (b) at least one external magnet configured to induce an external magnetic field and to be held externally to the skin of the user, facing a pre-determined location at the skin of the user, said pre-determined location at the skin of the user is facing a pre-determined location in the gastro-intestinal (GI) tract or in the stomach,
   wherein a magnetic axis of the at least one internal permanent magnet is perpendicular to a longitudinal axis extending through the capsule, wherein the longitudinal axis is parallel to the elongated wall of the capsule,
   wherein the external magnetic field induced by the at least one external magnet is configured to capture and retain the capsule at the pre-determined location in the GI tract or in the stomach,
   wherein the one or more holes are configured to enable the drug to flow out from the capsule therethrough into GI fluid, and
   wherein predetermined changes in the direction of the external magnetic field induced by the at least one external magnet cause the at least one internal permanent magnet to flip over the capsule relative to a GI wall or a wall of the stomach, and wherein the flip is configured to control the flow of the drug through the one or more holes of the capsule, while maintaining its position within the GI or the stomach.

2. The drug delivery system of claim 1, wherein the flip is configured to transition the capsule between a state (a) and a state (b), wherein:
   in state (a) the one or more holes of the capsule located at the first side of the elongated wall thereof are sealed and blocked by the GI wall or the wall of the stomach, thereby blocking the flow of the drug out from the capsule; and
   in state (b) the second opposing side of the elongated wall of the capsule is facing the GI wall or the wall of the stomach, so that the one or more holes of the capsule are not sealed against the GI wall or the wall of the stomach, thereby enabling the flow of the drug out from the capsule and into the GI fluid.

3. The drug delivery system of claim 2, wherein flipping over the at least one external magnet changes the direction of the external magnetic field.

4. The drug delivery system of claim 3, further comprising an automatic control system configured to flip over the at least one external magnet.

5. The drug delivery system of claim 1, further comprising a belt attached to a device, the device comprising the at least one external magnet, and is configured to attach the at least one external magnet to the skin.

6. The drug delivery system of claim 5, wherein the device further comprises a processor and a mechanical driver, wherein the drug delivery system further comprises a sensor comprising accelerometers and inclinometers wrapped around a wrist of the user and connected by an electric cable to the device, wherein the sensor is configured to send signals that represent the mechanical motion of the arm of the user to the processor, wherein the processor is configured to detect physiological signals that indicate the level of the drug in the blood of the user and to send commands to the mechanical driver, and wherein the mechanical driver is configured to control release of the drug from the capsule by inducing a change in direction of the external magnetic field through the at least one external magnet.

7. The drug delivery system of claim 1, wherein the at least one external magnet is an electromagnet, configured to induce the external magnetic field, and wherein the electromagnet is configured to flip the capsule when current flowing within the electromagnet changes direction.

8. The drug delivery system of claim 1, wherein the at least one external magnet is an electropermanent magnet.

9. The drug delivery system of claim 8, wherein the electropermanent magnet is configured to cause the capsule to vibrate by modulating the external magnetic field at a predetermined frequency, wherein the predetermined frequency is in the ultrasound range or in the resonance frequency range of a gastrointestinal area, and wherein the drug delivery system further comprises a vibration sensor attached to the at least one external magnet, configured to pick a vibration signal of the capsule.

10. The drug delivery system of claim 8, wherein the electropermanent magnet is configured to modulate the external magnetic field in pulses.

11. The drug delivery system of claim 8, further comprising a driver configured to generate a sinusoidal signal to increase or decrease the external magnetic field of the electropermanent magnet, wherein the drug delivery system further comprises: a vibration sensor attached to the at least one external magnet, a filter configured to filter sound signals received from the vibration sensor, an amplifier configured to amplify the filtered signals from the filter, and a phase comparator configured to receive driving signals from the driver and amplified signals from the amplifier.

12. The drug delivery system of claim 2, further comprising a sleeve surrounding the capsule, wherein the sleeve is made of an elastic material, wherein during state (a) the one or more holes of the capsule are sealed and blocked against a wall of the sleeve, and wherein during state (b) the one or more holes are not sealed against the wall of the sleeve.

13. A method for controlled drug release comprising the steps of:
   a) providing the drug delivery system according to claim 2 to a user;
   b) the user swallowing the capsule;
   c) holding the at least one external magnet externally to the skin of the user facing a pre-determined location at the skin of the user, wherein said pre-determined location at the skin of the user faces a pre-determined location in the GI tract or in the stomach, thereby capturing and retaining the capsule at the pre-determined location; and
   d) inducing predetermined changes in the direction of the external magnetic field of the at least one external magnet, such that the capsule transitions between state (a) and state (b), thereby enabling the flow of the drug out from the capsule and into the GI fluid.

14. The method of claim 13, wherein the at least one external magnet is a permanent magnet, and wherein step (d) of inducing predetermined changes in the direction of the external magnetic field comprises flipping over the at least one external magnet relative to the skin of the user.

15. The method of claim 13, wherein the at least one external magnet is an electromagnet, and wherein step (d) of inducing predetermined changes in the direction of the external magnetic field comprises changing the current flow direction of the electromagnet.

16. A drug delivery system comprising:
(a) a capsule configured to be swallowed by a user, the capsule comprising: a drug contained within the capsule, at least three internal magnets, at least two internal springs, one or more holes, and a flap that is connected to a ceiling of the capsule along one of the flap sides and is covering the one or more holes, wherein each internal spring is attached to the capsule and to at least one of the at least three internal magnets, wherein at least one of the at least three internal magnets is attached to a floor of the capsule, wherein the ceiling and the floor of the capsule are positioned in parallel to a longitudinal axis extending through the capsule; and
(b) at least one external magnet comprising an external spring connected thereto, wherein the at least one external magnet is configured to induce an external magnetic field,
wherein the at least one external magnet is configured to be held externally, facing a pre-determined location at the skin of a user, said pre-determined location at the skin of the user faces a pre-determined location in the GI tract or in the stomach, wherein the external magnetic field induced by the at least one external magnet is configured to capture and retain the capsule at the pre-determined location in the GI tract or in the stomach, wherein the capsule is retained so that the floor of the capsule is facing the pre-determined location in the GI tract or in the stomach,
wherein the at least one external magnet is configured to be separated from the skin of the user by the external spring, wherein in a closed state of the flap, no drug is flowing out of the capsule,
wherein the external magnetic field induced by the at least one external magnet increases when the external spring is pressed towards the body, and
wherein at least one of the at least three internal magnets is configured to react to the increased magnetic field induced by the at least one external magnet, thereby pressing at least one of the at least two internal springs, resulting in pushing the flap from the closed state to induce the flow of the drug out from the capsule, through the one or more holes and the flap, into GI fluid.

17. The drug delivery system of claim 16, wherein the capsule comprises two internal springs, wherein the at least three internal magnets comprise: a main internal magnet attached to the floor of the capsule and two secondary internal magnets, wherein each one of the two secondary internal magnets is attached to the ceiling of the capsule at one end and to each one of the two internal springs at the other end, respectively, wherein each one of the two internal springs is connected to the floor of the capsule or to the main internal magnet at the other end, wherein the two secondary internal magnets are configured to react to the increased magnetic field induced by the at least one external magnet, thereby pressing each one of the two internal springs, respectively, towards the floor of the capsule, in order to reduce the volume of the capsule resulting in the flow of the drug out from the capsule through the one or more holes and the flap into GI fluid.

18. The drug delivery system of claim 16, further comprising a belt attached to a device, the device comprising the at least one external magnet and the external spring connected thereto, wherein the device is configured to hold the at least one external magnet separated from the skin of the user by the external spring.

19. The drug delivery system of claim 16, wherein the external spring is a compressible layer of foam, and wherein each one of the at least two internal springs is a compressible foam piece.

* * * * *